(12) United States Patent
Merki et al.

(10) Patent No.: US 7,140,253 B2
(45) Date of Patent: Nov. 28, 2006

(54) DEVICE FOR THE ULTRASOUND MEASURING OF CYLINDRICAL TEST MODELS

(75) Inventors: Hubert A. Merki, Brewster, NY (US); Sven Naegeli, Putnam Valley, NY (US); James Daleo, Brewster, NY (US)

(73) Assignee: Zumbach Electronic AG, Orpund (CH)

( * ) Notice: Subject to any disclaimer, the term of this patent is extended or adjusted under 35 U.S.C. 154(b) by 0 days.

(21) Appl. No.: 10/871,276

(22) Filed: Jun. 21, 2004

(65) Prior Publication Data

US 2004/0255677 A1 Dec. 23, 2004

(30) Foreign Application Priority Data

Jun. 23, 2003 (EP) .................................. 03014068

(51) Int. Cl.
*G01N 29/04* (2006.01)
(52) U.S. Cl. .............................. 73/620; 73/622; 73/632
(58) Field of Classification Search ................. 73/618, 73/622, 625, 626, 627, 1.86, 620, 623, 629, 73/632
See application file for complete search history.

(56) References Cited

U.S. PATENT DOCUMENTS

| | | | |
|---|---|---|---|
| 2,961,635 A * | 11/1960 | Trott | ........................... 367/155 |
| 4,114,456 A | 9/1978 | Dory | |
| 4,254,660 A | 3/1981 | Prause | |
| 4,620,463 A * | 11/1986 | Horn et al. | ................... 82/1.11 |
| 5,085,567 A * | 2/1992 | Neumann, Ulrich | ......... 425/71 |
| 5,388,976 A * | 2/1995 | Kruger et al. | .............. 425/141 |
| 5,531,124 A * | 7/1996 | Kim et al. | ............... 73/861.27 |
| 6,634,233 B1* | 10/2003 | He | ............... 73/597 |
| 6,935,178 B1* | 8/2005 | Prause | ........................ 73/622 |
| 2002/0134159 A1 | 9/2002 | He | |

FOREIGN PATENT DOCUMENTS

DE   33 03 637 A1   8/1984

OTHER PUBLICATIONS

"The Tube Inspection System", Danish Atomic Energy Commission, pp. 2-4, 8-9 and 11, (Aug. 1982), Denmark.

* cited by examiner

*Primary Examiner*—Hezron Williams
*Assistant Examiner*—Jacques M. Saint-Surin
(74) *Attorney, Agent, or Firm*—Venable LLP; Robert Kinberg; Steven J. Schwarz

(57) ABSTRACT

A device is provided for the ultrasonic measuring of cylindrical test specimen, in particular tubes and hoses, wherein said device can be filled with water or submerged in a water bath and is provided with at least one ultrasonic measuring head secured on the device. The device is characterized by a cylindrical reference mandrel, the longitudinal axis of which at least essentially coincides with the measuring axis of the device, and at least one cylindrical auxiliary mandrel that extends parallel to the reference mandrel, can be moved to a position between the ultrasonic measuring head and the reference mandrel, and can also be removed from this position.

11 Claims, 5 Drawing Sheets

DEVICE FOR THE ULTRASOUND MEASURING OF CYLINDRICAL TEST MODELS

CROSS-REFERENCE TO RELATED APPLICATION

This application claims the priority of European Patent Application No. 03014068.5, filed Jun. 23, 2003, the subject matter of which is incorporated herein by reference.

BACKGROUND OF THE INVENTION

The invention relates to a device for the ultrasonic measuring of cylindrical test specimen, in particular tubes and hoses, wherein this device can be filled with water or submerged in a water bath and is provided with at least one ultrasonic measuring head. The invention furthermore relates a corresponding method.

Tubes and hoses made from plastic or metal are normally produced with the extrusion method, for which the plastic or the metal is pressed through an extrusion die and/or nozzle that determines the dimensions of the extruded product. Different factors such as temperature, pressure, mass flow, discharge speed and setting errors of the extruding equipment, just to name a few, influence the quality of the end product and can, for example, lead to deviations in the cross-sectional geometry.

Various methods are known already for measuring the extruded products, either in-line or with the aid of test specimen in the test laboratory where mechanical micrometers and optical measuring devices are mainly used.

Profile projectors are frequently used with the optical measuring instruments, which project the shadow of the cross-sectional pattern to be measured onto a screen where it can be measured.

Reference DE 33 03 637 A1 discloses a device for measuring the cross-sectional dimensions of hollow-cylindrical work pieces. For this, a work piece test specimen to be measured is centered relative to three end positions that are arranged in a triangle with uniform legs on the test specimen wall and two diametrically opposite arranged measuring systems are arranged on the center perpendicular line for the connecting line between the two other end stops on the outside wall of the test specimen. The end position on the inside in this case is a rotating, cylindrical holding mandrel with a defined diameter and a horizontal center axis, wherein the inside wall of the test specimen rests in the manner of a line on this holding mandrel.

With this known device, the preparations for obtaining the desired measuring results are very involved and measuring errors can also occur easily.

Furthermore known is a method for determining the wall thickness of tubes and hoses and/or hollow cylindrical work pieces in the production line or the test laboratory with the aid of ultrasonic measuring. Thus, a printed article by the Danish Atomic Energy Commission, entitled "Tube Inspection System," describes a measuring device for tubes where the wall thickness of a tube is measured from the outside only with the aid of ultrasound and two opposite arranged, non-contacting sensors.

However, the measuring with the aid of ultrasound was not precise enough for laboratory measurements, primarily because of the direct dependence of the measurement on the sonic speed of the material and its temperature dependence.

A device and a method for determining the wall thickness and sonic speed with the aid of reflected ultrasonic pulses is known from U.S. Patent Application No. 2002/0134159 A1. The content of this published patent application mostly coincides with the explanations provided in the scientific article published by Ping He "Simultaneous measurement of sound velocity and wall thickness of a tube," in: Ultrasonics 39 (2001), 407–411, Elsevier Science B.V. The device described therein is shown in FIG. 1, which will be explained in further detail later on. The article suggests using the distance between the two ultrasonic measuring heads used as reference value. However, it has turned out that this reference is relatively unstable, wherein the opposite-arranged measuring head surfaces appear to be responsible for the unstable reflections.

As in the latter case, the ultrasonic measurement according to our invention is carried out with water as the coupling medium. The test specimen is submerged for this purpose in a water bath, in which at least some parts of the measuring device, e.g. the ultrasonic measuring heads, are also located. With an ultrasonic measuring in line, the tube to be measured is normally pulled through the water bath.

SUMMARY OF THE INVENTION

It is the object of the present invention to provide a device and a method for the ultrasonic measuring of cylindrical test specimen, which makes it possible to determine several test specimen parameters simultaneously and with higher accuracy than has been possible so far.

This object is solved with a device for the ultrasonic measuring of cylindrical test specimen, in particular tubes and hoses, wherein said device can be filled with water or can be submerged in a water bath and is provided with at least one ultrasonic measuring head secured to the device, characterized by a cylindrical reference mandrel, the longitudinal axis of which coincides at least essentially with the measuring axis of the device, and at least one cylindrical auxiliary mandrel which extends parallel to the reference mandrel, can be moved to a position between the ultrasonic measuring head and the reference mandrel, and can also be removed again from this position.

The generally known technique of ultrasonic measuring is used with the device and the method according to the invention. An ultrasonic wave is either reflected at the boundary layer of two mediums or penetrates this boundary layer. For an ultrasonic measurement, the ultrasonic transit time is determined, starting with the ultrasonic signal that is emitted by the ultrasonic measuring head to the moment when an ultrasonic echo that is reflected at a boundary surface is received. Dividing this time value in half makes it possible to obtain the transit time for this ultrasonic signal from the ultrasonic measuring head to the boundary surface where the reflection occurred. The expression "transit time," used within the framework of the present application, represents this time value. An ultrasonic measurement is thus always a distance measured between the boundary surfaces of two or more mediums. The transit time for each medium is detected during the ultrasonic measurement. If this transit time is multiplied by the sonic speed, the thickness of the respective layer is obtained.

The ultrasonic measuring device according to the invention is provided with a holder for at least one ultrasonic measuring head. The device according to the invention can have a pot-shaped design, for example, wherein at least one ultrasonic head is arranged and secured in the side wall. The test specimen to be measured in that case is located on the inside of this "pot" filled with water. The water represents the coupling medium for the ultrasound. However, it is also possible to submerge the device according to the invention in a water bath or the like and to secure the ultrasonic measuring heads in an optional manner.

The device according to the invention distinguishes itself among other things by a cylindrical reference mandrel having a longitudinal axis that coincides at least essentially and preferably exactly with the measuring axis of the device. This reference mandrel is smaller than the smallest inside diameter of the test specimen to be measured. The reference mandrel diameter is a known value that can be determined in a suitable and known manner, for example with an optical measurement or also a mechanical measurement by using a slide rule or the like. The measuring axis represents the center axis for the ultrasonic measuring device according to the invention. For the measuring of the test specimen, which will be discussed in further detail later on, the test specimen should be centered and oriented if possible in such a way that the longitudinal axis of the tube-shaped and/or cylindrical test specimen coincides with the measuring axis. In addition to the reference mandrel, the device according to the invention is distinguished by at least one cylindrical auxiliary mandrel that extends parallel to the reference mandrel. The diameter of this auxiliary mandrel is preferably also known or can be determined precisely in the standard manner. The reference mandrel as well as the auxiliary mandrel in this case are solid rods, preferably with the same diameter.

Together with the reference mandrel, the auxiliary mandrel is used to calibrate the device according to the invention because the measuring accuracy of an ultrasonic measuring device depends on the calibration. The fact that the origin of the sonic wave in an ultrasonic measuring head cannot be determined precisely geometrically is a problem and requires a special calibration and/or calibration procedure. A special calibration and/or a special calibration procedure of this type is possible with the device according to our invention.

For this calibration, the auxiliary mandrel is moved to a position between the ultrasonic measuring head and the reference mandrel and the calibration steps carried out which are described in further detail in the following.

The auxiliary mandrel is removed for the measuring of the test specimen and the specimen pushed onto the reference mandrel, such that the longitudinal axis of the test specimen coincides if possible with the measuring axis and also the longitudinal axis of the reference mandrel. For this, the test specimen should be submerged completely in water, so that the inside space of the test specimen is also filled with water.

According to one preferred embodiment, 2, 3, 4, 5, 6 or more ultrasonic measuring heads exist, wherein an even number of measuring heads is advantageous. Respectively two measuring heads are preferably positioned diametrically opposite each other relative to the measuring axis. The ultrasonic measuring heads advantageously are oriented in a joint plane. One preferred embodiment is provided with 4 ultrasonic measuring heads, which are mounted and oriented at an angle of 90° relative to each other. Thus, pairs of ultrasonic measuring heads are always positioned opposite each other on an axis which is perpendicular to the measuring axis.

The ultrasonic measuring heads are connected to a signal processor which evaluates the measured signals and converts the obtained values into distances, wherein the measuring results can be supplied via a suitable interface to a computer.

The device according to the invention can be designed in such a way that it has only one auxiliary mandrel which can be moved and positioned between all existing ultrasonic measuring heads and the reference mandrel. This auxiliary mandrel can be displaced advantageously along a circular path around the center axis. This can be realized, for example, by mounting the auxiliary mandrel on a preferably disk-shaped holding device, provided with a through bore in the center for accommodating the reference mandrel, thus allowing it to rotate around the reference mandrel and also around the center axis. Of course, the holding device can also be provided with several auxiliary mandrels and is removed from the device following the calibration.

For measuring the test specimen, a holder with a through bore for the reference mandrel is pushed onto this reference mandrel and is inserted into the device. This holder preferably consists of two holding parts, namely a lower and an upper holding part, which have an approximately trapezoid shape as seen in a longitudinal section and are rotation-symmetrical. In other words, these holding parts have approximately the form of a truncated cone, provided with a through bore in the center for fitting them onto the reference mandrel. In addition, these holding parts are mounted such that the truncated cones face each other and, depending on the inside diameter of the test specimen, project into the test specimen. In the process, the ends of the cylindrical test specimen come to rest against the inclined planes of the truncated cone shape and are centered and oriented concentrically to the center axis.

The following parameters of cylindrical test specimen, for example tubes and hoses, can be determined with the device according to the invention: outside diameter, inside diameter, as well as average value, minimum, maximum and eccentricity of the wall thickness.

These parameters can be determined simultaneously in seconds by submerging the test specimen once. For the total wall thickness of the test specimen, measuring accuracies in the order of magnitude of a few micrometers can be achieved.

One problem, however, is that the reflection point on a cylinder depends on its radius of curvature and the sound-radiating characteristic of the ultrasonic measuring head. For that reason, the respective calibration curves must take this effect into account.

It has turned out that the distance measurements are influenced to a small but for many applications significant degree by the radius of the test specimen. The distance measured to a flat surface is shorter than the same distance to a cylindrical test specimen, wherein this relation approximately corresponds to a linear function to the test specimen diameter.

This characteristic must be taken into account for the calibration as well as for the measurement to obtain precise results. A similar problem exists if the distance to a concave surface must be detected. In that case, the distance appears to be shorter.

The correction made necessary by different radii is determined by measuring different standards, starting with the reference mandrel as such, up to the maximum diameter permitted by the device according to the invention for a test specimen to be measured. The measuring differences are detected and can be expressed in a table or a formula and can be considered accordingly during a measuring operation.

The subject matter of our invention furthermore is a method for the ultrasonic measuring of cylindrical test specimen in water, in particular tubes and hoses. A cylindrical test specimen is measured for this with the aid of an ultrasonic signal emitted by at least one ultrasonic measuring head in an ultrasonic measuring device. With this method, the device is first calibrated and the test specimen is then measured.

The calibration requires the following steps:

a) A cylindrical auxiliary mandrel with known diameter is moved inside the device to a position between the ultrasonic measuring head and a cylindrical reference mandrel with known diameter, for which the longitudinal axis coincides at least essentially with the measuring axis for the device.

b) The distance D3 between the outside jacket surface of the auxiliary mandrel, pointing toward the ultrasonic measuring head, to the outside jacket surface of the reference mandrel is measured in a manner known per se, for example mechanically or optically, provided the distance D3 is not already known.

c) To obtain the distance D5 from the ultrasonic measuring head to the reference mandrel, the transit time for an ultrasonic echo is measured in water while the auxiliary mandrel is removed.

d) If the auxiliary mandrel is positioned between the reference mandrel and the ultrasonic measuring head, the transit time for an ultrasonic echo is measured in water to obtain the distance D4 between the ultrasonic measuring head and the opposite-arranged outer jacket surface of the auxiliary mandrel.

e) By taking into account the transit time values, measured for the distances D4 and D5, as well as the distance value D3, the distance D5 from the outside jacket surface of the reference mandrel to the virtual sound origin in the ultrasonic measuring head is computed as reference distance D5, as length dimension.

The following steps are realized for the measuring operation:

f) By taking into account the reference distance D5 from the virtual sound origin to the reference mandrel, known from step e), the current sonic speed in water is determined while no test specimen is located inside the measuring device.

g) The test specimen must be inserted into the device in such a way that it rotates concentrically if possible around the reference mandrel.

h) For at least one boundary surface of the test specimen, an ultrasonic echo is measured for the distance between this boundary surface and the virtual sound origin in the ultrasonic measuring head.

i) At least one desired parameter of the test specimen is then computed from the determined data.

If a device has been calibrated once with a given reference mandrel, it is normally sufficient to realize only the steps f) to i), wherein the parameter determined for the test specimen preferably is the wall thickness.

BRIEF DESCRIPTION OF THE DRAWINGS

The invention is explained in further detail in the following with the aid of the attached drawings, which schematically show a device according to the invention that is not true to scale. The same parts are given the same reference numbers in the drawings, wherein the drawings show in.

DETAILED DESCRIPTION OF THE INVENTION

Figure 1:
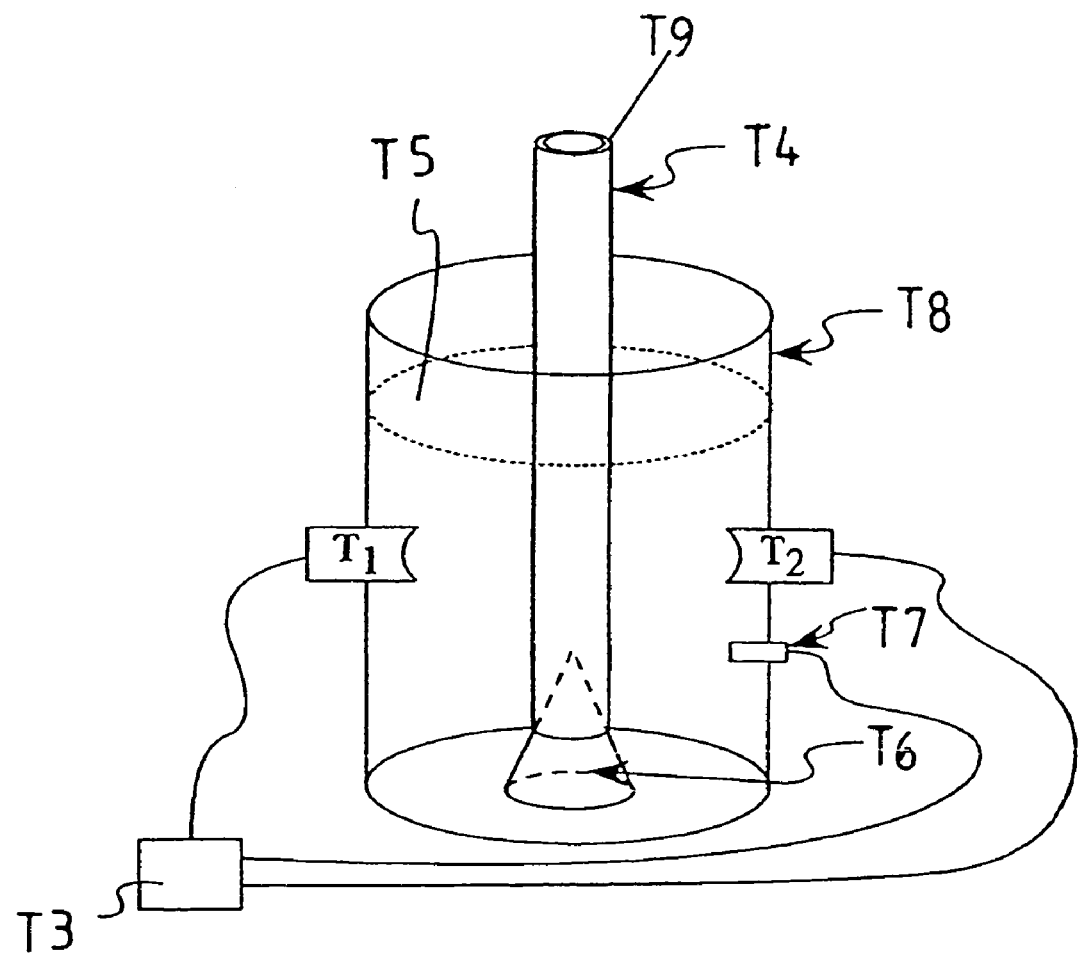
FIG. 1 A schematic perspective view of a device, known from reference U.S. No. 2002/0134159 A1, for the ultrasonic measuring of a cylindrical test specimen, in particular a tube.

The device shown in FIG. 1 comprises a measuring chamber for determining the wall thickness of a tube-shaped object with the aid of ultrasonic measuring. This measuring chamber is known from and is described in reference U.S. No. 2002/0134159 A1.

The known measuring chamber T8 (the reference numbers used to explain prior art are provided with a "T" in front of the actual number) is filled with a typical coupling medium T5, which normally is water. The tube-shaped object T4 to be measured is fitted in the measuring chamber T8 onto a cone-shaped centering device T6, so that the tube-shaped test specimen T4 is positioned in the center of the measuring chamber T8. Two diametrically opposite-arranged ultrasonic measuring heads T1 and T2 for sending out and receiving ultrasonic pulses are installed in the measuring chamber T8. The wall thickness T9 of the tube-shaped test specimen T4 is determined with the aid of these two ultrasonic measuring heads T1 and T2 and the resulting data are then supplied to an electronic unit T3 where they are processed. These data also include the temperature data determined with a temperature sensor T7.

Figure 2:
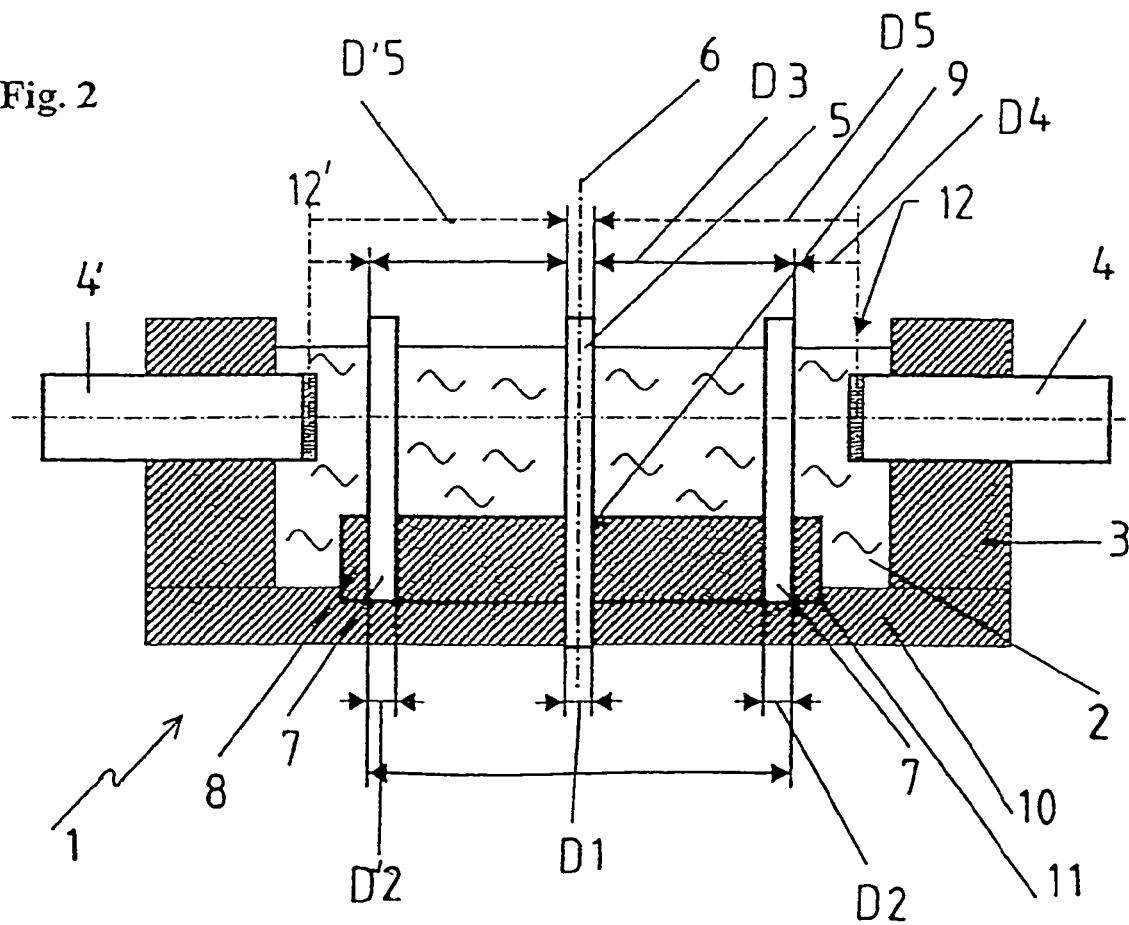
FIG. 2 A basic longitudinal section, shown schematically, of a device according to the invention, in the calibrated state.

FIG. 2 shows a longitudinal sectional view through a device according to the invention for the ultrasonic measuring of cylindrical test specimen. The device according to the invention has a test chamber 2 that is filled with water. The test chamber 2 has a circumferential side wall 3 with two ultrasonic measuring heads 4, 4' arranged and secured diametrically opposite each other. These ultrasonic measuring heads 4, 4' are of a known type and nature and will not be described further herein.

A cylindrical reference mandrel 5, for which the longitudinal axis coincides with the measuring axis 6 of the device 1 and/or the measuring chamber 2, is arranged in the center of the measuring chamber 2, between the two ultrasonic measuring heads 4, 4'.

This reference mandrel 5 is a solid metal cylinder, wherein the diameter of this reference mandrel 5 has a specific value given the reference D1. The diameter D1 of reference mandrel 5 is a known value that can be determined precisely either mechanically or in other ways.

An auxiliary mandrel 7 which is also a solid metal cylinder with exactly known diameter D2, is arranged so as to be aligned between the ultrasonic measuring head 4 and the reference mandrel 5. This auxiliary mandrel extends parallel to the reference mandrel 5 between the ultrasonic measuring head 4 and the reference mandrel 5 and is secured with its lower end in a holding device 8. The diameter of reference mandrel 5 in this case corresponds to the diameter of the auxiliary mandrel 7. The holding device 8 is a disc with a bore 9 in the center through which the reference mandrel 5 extends into a receptacle in the base 10. The reference mandrel 5 is thus secured in the base 10.

The disc-shaped holding device 8 is inserted into a disc-shaped indentation 11 and can be removed by pulling it up and out of the indentation 11 as well as the measuring chamber 2, wherein the reference mandrel 5 slides through the bore 9.

The simplest design of the device 1 according to the invention is provided with only one ultrasonic measuring head 4, whereas a preferred embodiment of the device 1 is provided with at least one pair of ultrasonic measuring heads 4, 4' which furthermore are advantageously arranged diametrically opposite each other, as shown in FIG. 2. In that case, the reference mandrel is arranged in the center between both ultrasonic measuring heads 4, 4' which can emit ultrasonic signals and/or pulses in the direction of the reference mandrel 5. With the device 1 shown in FIG. 2, an auxiliary mandrel 7 is furthermore positioned between the second ultrasonic measuring head 4' and the reference mandrel 5. This auxiliary mandrel 7 is an additional auxiliary mandrel 7 which is designed and embodied in the same way as the above-described auxiliary mandrel 7, meaning two auxiliary mandrels 7 are inserted into the disc-shaped holding device 8. The holding device 8 can be provided with only one auxiliary mandrel 7 which is moved along a circular path around the measuring axis 6, and thus around the longitudinal axis for the reference mandrel 5, by allowing the holding device 8 to rotate around the measuring axis 6 and thus the reference mandrel 5.

The calibration of the device according to the invention is explained in further detail in the following with reference to the ultrasonic measuring head 4. The other ultrasonic measuring heads 4' etc. are calibrated in the same way, as will be explained further in the following.

If the auxiliary mandrel 7 is positioned between the reference mandrel 5 and the ultrasonic measuring head 4, then the distance and/or the spacing D3 from the outer jacket surface of the auxiliary mandrel 7, pointing toward the ultrasonic measuring head 4, to the outer jacket surface of the reference mandrel 5 is also known, wherein this distance D3 can be determined mechanically without problems. All mechanical and thus easily determined distances D1, D2 and D3 are shown in FIG. 2 with continuously drawn lines.

During the calibration operation, an ultrasonic signal is first transmitted by the ultrasonic measuring head in the direction of the auxiliary mandrel 7, is then reflected and received by the ultrasonic measuring head 4. The received signal and/or the transit time obtained in this way corresponds to the distance D4 and thus the spacing between the ultrasonic measuring head 4 and the outside jacket surface of the auxiliary mandrel 7 that faces the ultrasonic measuring head.

Following this, the auxiliary mandrel 7 is removed and a different ultrasonic measurement carried out to determine the distance D5 and thus the spacing between the outside jacket surface of the reference mandrel 5 and the ultrasonic measuring head 4. The resulting transit time for the ultrasonic echo corresponds to the distance D5.

The purpose of this calibration is to determine the precise distance between the virtual sound origin 12 and the reference mandrel 5 because this virtual sound origin 12 is located inside the ultrasonic measuring head 4, but cannot be determined easily in a mechanical way or in any other way.

From the mechanically determined values and the received ultrasonic echoes, the precise distance between the virtual sound origin 12 and the outside jacket surface of the reference mandrel 5 can then be determined by means of a simple three-column computation because the distance D3 has been determined and the distance D5 represents the sum of D3 and D4. For a given device and/or for a given ultrasonic measuring head 4, the distance D5 is then fixed, meaning independent of the temperature of the coupling medium water, etc.

The same type of calibration is carried out for the other ultrasonic measuring head 4' or the additional ultrasonic measuring heads.

If the ultrasonic measuring heads 4, 4' are positioned diametrically opposite each other, then the reference diameter (more precisely the distance from the virtual sound origin 12 of the ultrasonic measuring head 4 to the virtual sound origin 12' of the opposite arranged ultrasonic measuring head 4') is fixed. This distance corresponds to the sum of D5+D'5+D1, wherein D'5 is the distance between the virtual sound origin 12' and the outside jacket surface of reference mandrel 5.

Figure 3:
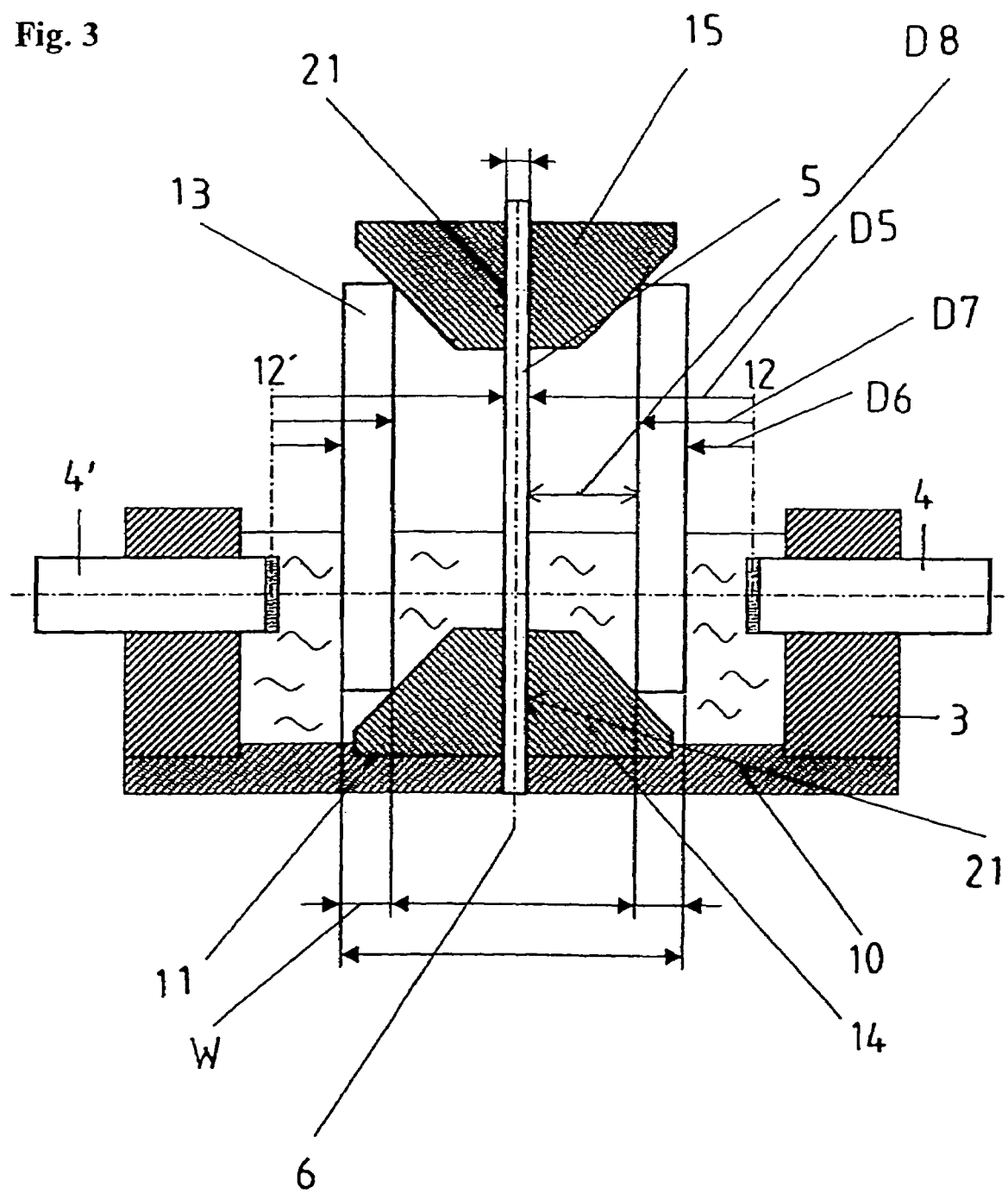
FIG. 3 A view of the device as shown in FIG. 2, in the state where a test specimen is measured.

For measuring a test specimen 13, the holder 8 together with the auxiliary mandrel 7 or the auxiliary mandrels 7, disposed therein, is removed by pulling it upward and out of the measuring chamber 2. In the process, the reference mandrel 5 slides through the bore 9. Following this, a holder 14 with central bore 21 is fitted onto the reference mandrel 5 and pushed down far enough so that it comes to rest in the depression 11. This situation is shown in FIG. 3. The holder 14 has an approximately trapezoid cross-sectional shape and is designed to be rotation-symmetrical to the measuring axis 6. The test specimen 13 is then fitted with one of its ends onto the holder 14, meaning onto the conically tapered side surfaces of the aforementioned trapeze. As a result, the test specimen is centered around the measuring axis 6, such that it extends approximately concentric thereto. At the upper end 13, a holder 15 that corresponds to the holder 14 is furthermore fitted upside down onto the test specimen 13 and the reference mandrel 5.

During the subsequently realized ultrasonic measurement with inserted test specimen, the transit times $t'_{D5}$, $t'_{D6}$ and $t'_{D7}$ are measured to obtain the distances D5, D6 and D7. The reference distance D5 as length dimension is known from the calibration operation. Just prior to inserting the test specimen into the device 1 and submerging it into water, the sonic speed in the water to be used was determined as with the following equation:

$$v_w = D5/t_{D5}$$

The sonic speed in water can also be determined following the measuring operation with the inserted test specimen 13.

The distances in water with inserted test specimen 13 are then computed as follows:

$$D6 = v_w \cdot t'_{D6} = D5(t'_{D6}/t_{D5})$$

$$D8 = D5 - D7 = v_w(t'_{D5} - t'_{D7})$$
$$= D5[(t'_{D5} - t'_{D7})/t_{D5})$$

The wall thickness w of the test specimen 13 is then computed as follows:

$$W = D5 - (D8 + D6).$$

D8 in this case represent the distance from the outside jacket surface of the reference mandrel 5 to the opposite-arranged inside jacket surface of the test specimen 13.

Figure 5:
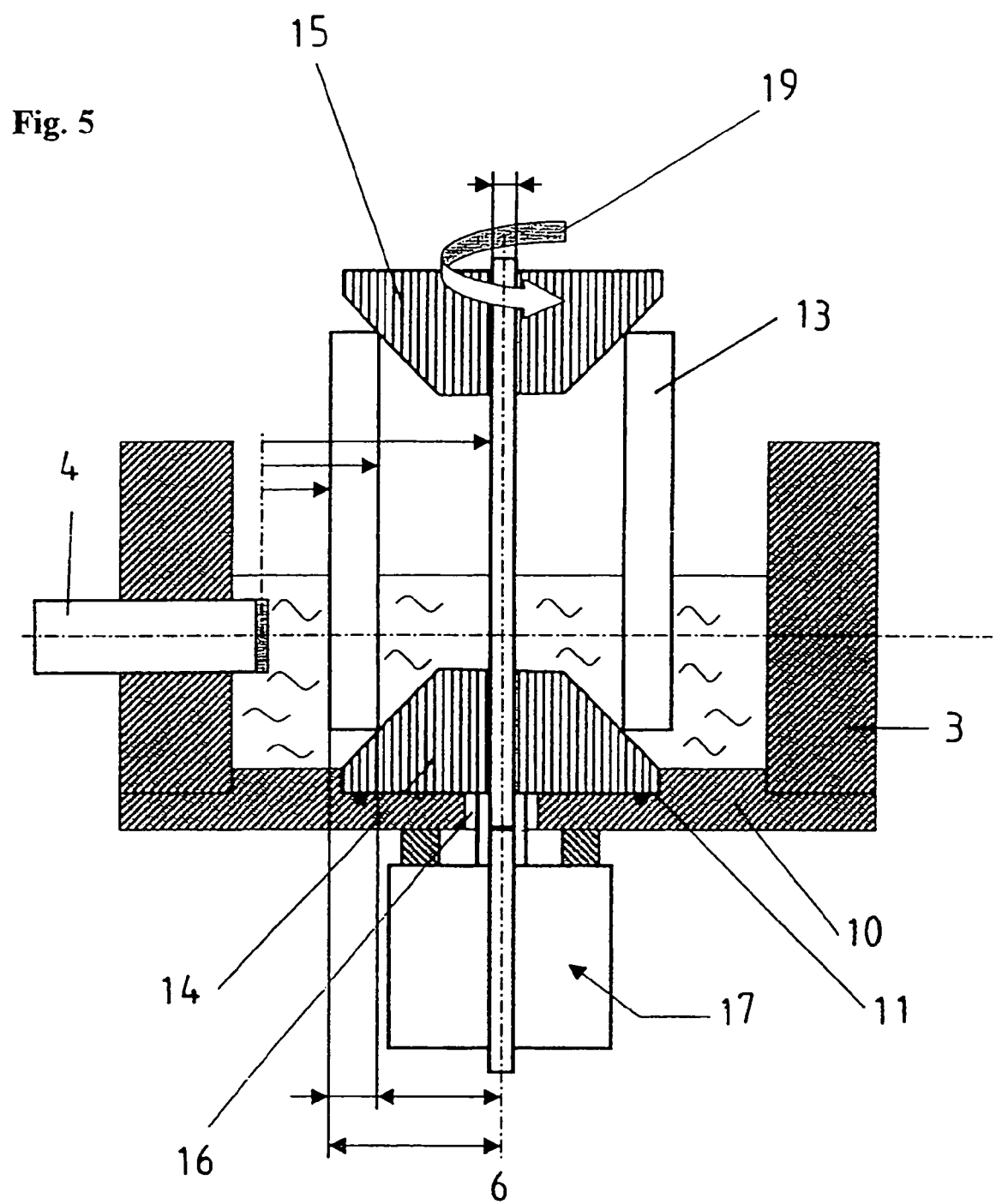
FIG. 5 An analog view to FIG. 3 with a different embodiment, comprising a test specimen held inside a rotating holder, and only one ultrasonic measuring head.

With the embodiment shown in FIG. 5, the holder 14 and the upper holder 15 are designed and positioned so as to rotate around the measuring axis 6, as indicated with arrow 19. The reference mandrel 5 is extended for that purpose through the base 10 and is rotated with the aid of a motor 17 that is arranged below the base 16 and is provided with an angle transmitter. The test specimen 13 can thus be measured across the complete circumference with only one ultrasonic measuring head 4.

Figure 4:
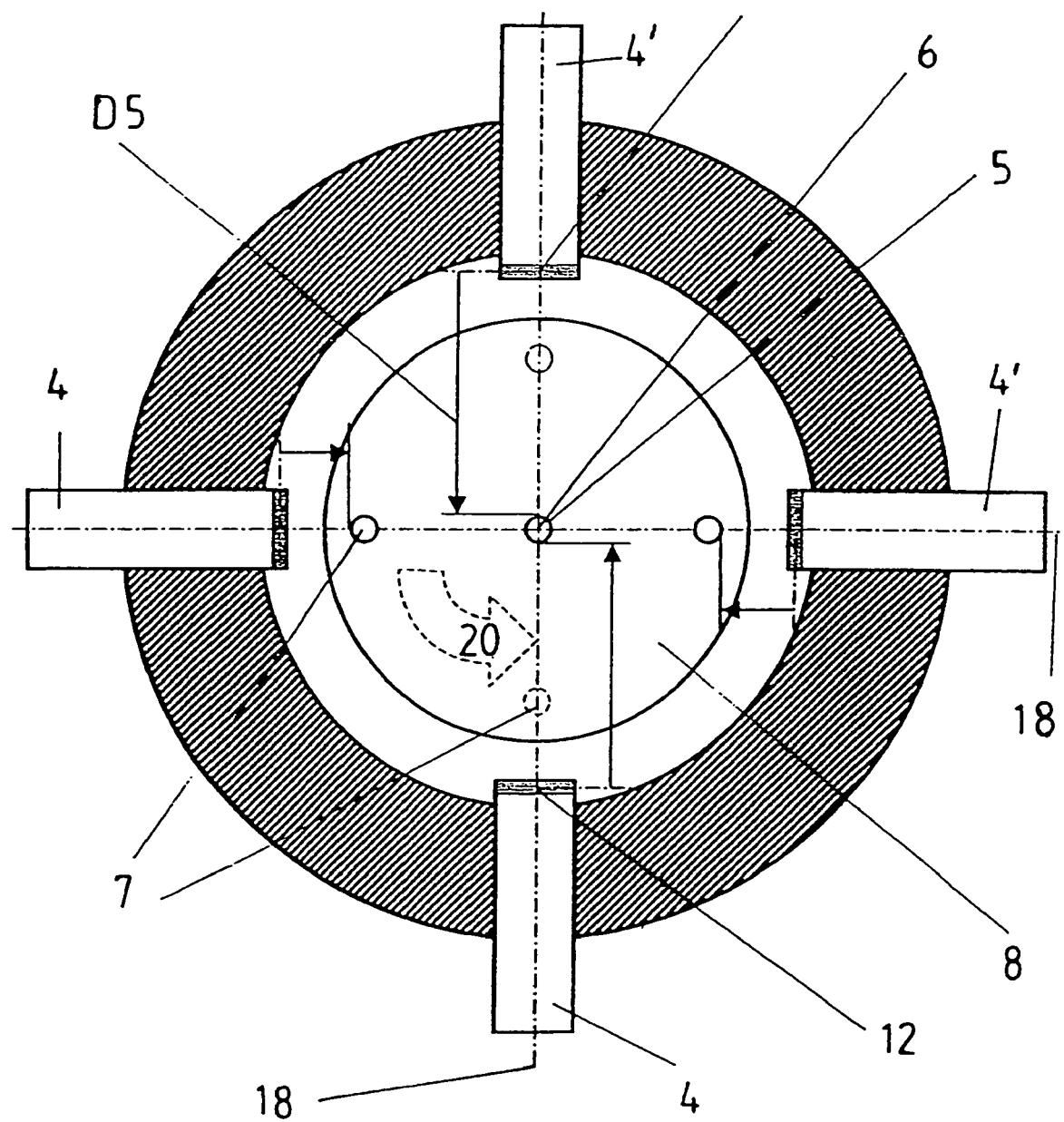
FIG. 4 A schematic basic view from above of the device shown in FIG. 2 with 4 ultrasonic measuring heads and several auxiliary mandrels.

FIG. 4 shows a view from above of a device according to the invention, comprising two pairs of ultrasonic measuring heads 4, 4' that are arranged at an angle of 90° around the reference mandrel 5. In other words, the connecting lines 18 for these two pairs of ultrasonic measuring heads 4, 4' are perpendicular to each other. The disk-shaped holding device 8 can be rotated around the measuring axis 6 and also around the reference mandrel 5 and is provided with two auxiliary mandrels 7. By turning the holding device 8 in the direction of arrow 20, the auxiliary mandrels 7 can be moved from the position between the ultrasonic measuring heads 4, 4', shown with continuous line, to a position between the other pair of ultrasonic measuring heads 4, 4'. This position is shown with dashed line. Following the previously described calibration operation, the holding device 8 is removed and replaced with the holder 14, 15 for the test specimen 13.

For all above-described devices 1, the ultrasonic measuring heads 4, 4' are connected to a signal processor which evaluates the measured signals and converts the obtained values into distances. The measuring results can be supplied via a suitable interface to a computer functioning as "user interface."

As described in the above, the wall thickness of the test specimen can be determined precisely with the aid of the device according to the invention, that is to say independent of the type of material used for the test specimen. The invention also permits measuring test specimen consisting of two or more layers and/or materials, for example toothpaste tubes and gasoline hoses which have two or more functional layers.

The total wall thickness of these test specimen can be determined precisely and independent of the material. Insofar as the sonic speed in the individual materials of a multi-layer test specimen is known, the device according to the invention can also be used to determine precisely the individual wall thickness and/or layer thickness. If the assumed sonic speed is not exactly correct for a specific material, the individual layer thickness determined according to the invention may not be correct either. However, since the total wall thickness is determined independent of the material, this error at most expresses itself in an incorrect ratio of the different wall thicknesses and/or layer thicknesses.

The invention has been described in detail with respect to exemplary embodiments, and it will now be apparent from the foregoing to those skilled in the art, that changes and modifications may be made without departing from the invention in its broader aspects, and the invention, therefore, as defined in the appended claims, is intended to cover all such changes and modifications that fall within the true spirit of the invention.

Reference Number List

| Prior Art | |
|---|---|
| T1, T2 | ultrasonic heads |
| T3 | electronic equipment |
| T4 | Tube-shaped test specimen |
| T5 | water/coupling medium |
| T6 | centering device |
| T7 | temperature sensor |

| Device according to the invention | |
|---|---|
| 1 | Device |
| 2 | measuring chamber |
| 3 | Side wall |
| 4, 4' | ultrasound measuring head |
| 5 | reference mandrel |
| 6 | measuring axis |
| 7 | auxiliary mandrel |
| 8 | Disc-shaped holding device |
| 9 | Bore |
| 10 | Base |
| 11 | Depression |
| 12 | virtual sound origin |
| 13 | Test specimen |
| 14 | holder (holding part), lower |
| 15 | holder (holding part), upper |
| 16 | Bore in the base |
| 17 | Motor |
| 18 | connecting line |
| 19 | Arrow |
| 20 | Arrow |
| 21 | central bore |
| D1 | diameter reference mandrel 5 |
| D2 | diameter auxiliary mandrel 7 |
| D3 | distance/spacing outside jacket surface reference mandrel 5 to outside jacket surface auxiliary mandrel 7 on the side facing the ultrasonic measuring head 4 |
| D4 | distance/spacing outside jacket surface for auxiliary mandrel 7 to opposite-arranged virtual sound origin 12 |
| D5, D5' | distance/spacing outside jacket surface for reference mandrel 5 to virtual sound origin 12 |
| D6 | distance/spacing outside jacket surface of test specimen 13 to opposite-arranged virtual sound origin 12 |
| D7 | distance/spacing from virtual sound origin 12 to the inside jacket surface of the test specimen 13, which faces the reference mandrel 5 |
| D8 | distance/spacing outside jacket surface for reference mandrel 5 to opposite-arranged outside jacket surface of test specimen 13 |
| W | wall thickness of test specimen 13 |

What is claimed is:

1. A device for ultrasonic measuring of a cylindrical test specimen located in a liquid medium, the device comprising:
   at least one ultrasonic measuring head;
   a cylindrical reference mandrel having a longitudinal axis that substantially coincides with the measuring axis of the device, the reference mandrel defining a fixed reference point with respect to the ultrasonic measuring head; and
   at least one cylindrical auxiliary mandrel that extends substantially parallel to the reference mandrel, wherein the auxiliary mandrel is movable along a substantially circular path around the reference mandrel in order to be removably positionable between the ultrasonic measuring head and the reference mandrel.

2. The device according to claim 1, comprising at least two ultrasonic measuring heads.

3. The device according to claim 2, comprising an even number of ultrasonic measuring heads wherein the ultrasonic measuring heads are arranged in pairs located diametrically opposite each other relative to the measuring axis.

4. The device according to claim 2, wherein the auxiliary mandrel is positionable between each of the ultrasonic measuring heads and the reference mandrel.

5. The device according to claim 2, comprising at least one auxiliary mandrel for each of the at least two measuring heads.

6. The device according to claim 1, further comprising a holder for the test specimen, wherein the at least one reference mandrel is removable from the device.

7. The device according to claim 1, further comprising at least one of a signal processor or a computer associated with the at least one ultrasonic measuring head.

8. The device of claim 1, further comprising a pot adapted to hold the liquid medium.

9. The device of claim 1, wherein the device is adapted to be submerged in the liquid medium.

10. A method of measuring a cylindrical specimen located in a liquid medium using an ultrasonic signal produced by at least one ultrasonic measuring head of a measurement device, the method comprising:

calibrating the measurement device using the following steps:

(a) measuring a first transmit time for an ultrasonic echo from the ultrasonic measuring head to a cylindrical reference mandrel located substantially coaxially with the measurement axis of the device;

(b) positioning a cylindrical auxiliary mandrel between the ultrasonic measuring head and the reference mandrel, and at a first known distance from the reference mandrel;

(c) measuring a second transmit time for an ultrasonic echo from the ultrasonic measuring head to the reference mandrel; and (d) calculating the distance from the ultrasonic measuring head to the cylindrical reference mandrel based on the first transit time, the second transit time, and the first known distance; and measuring the cylindrical specimen using the following steps:

(e) positioning the cylindrical specimen substantially coaxially around the reference mandrel;

(f) measuring a third transit time for an ultrasonic echo from the ultrasonic measuring head to a boundary surface of the specimen; and (g) calculating a dimensional property of the specimen based on at least the third transit time.

11. The method of claim 10, wherein once steps (a)–(d) have been carried out, only steps (e) to (g) need to be carried out to measure the cylindrical specimen.

* * * * *